(12) United States Patent
Macor et al.

(10) Patent No.: US 6,642,244 B2
(45) Date of Patent: Nov. 4, 2003

(54) PYRAZOLOPYRIDOPYRIMIDINE INHIBITORS OF CGMP PHOSPHODIESTERASE

(75) Inventors: John E. Macor, Flemington, NJ (US); Yingzhi Bi, Plainsboro, NJ (US)

(73) Assignee: Bristol-Myers Squibb Co., Princeton, NJ (US)

( * ) Notice: Subject to any disclaimer, the term of this patent is extended or adjusted under 35 U.S.C. 154(b) by 67 days.

(21) Appl. No.: 09/809,946

(22) Filed: Mar. 16, 2001

(65) Prior Publication Data

US 2002/0133008 A1 Sep. 19, 2002

(51) Int. Cl.⁷ .................... C07D 487/14; A61K 31/519; A61P 9/10; A61P 9/12; A61P 11/06
(52) U.S. Cl. ........................................ 514/267; 544/251
(58) Field of Search ................. 544/251, 267; 514/267

(56) References Cited

U.S. PATENT DOCUMENTS

| 5,716,993 A | 2/1998 | Ozaki et al. ................. 549/441 |
| 6,060,477 A | 5/2000 | Piazza et al. ................ 514/258 |
| 6,087,368 A | 7/2000 | Macor et al. ................ 544/251 |

FOREIGN PATENT DOCUMENTS

| DE | 3515882 A1 | 11/1986 |
| EP | 0054132 | 6/1982 |
| EP | 0210342 | 2/1987 |
| EP | 0347146 | 12/1989 |

OTHER PUBLICATIONS

Lucas et al. Pharmacological Reviews 52 (3), 375–413, 2000.*
Bi et al., Bioorganic & Medicinal Chemistry Letters, 11(18), 2461–2464, 2001.*
Dumaitre et al.; J. Med. Chem. 1996, 39, p. 1635–1644.

* cited by examiner

Primary Examiner—Richard L. Raymond
Assistant Examiner—Venkataraman Balasubramanian
(74) Attorney, Agent, or Firm—Stephen B. Davis

(57) ABSTRACT

Compounds of the formula (I)

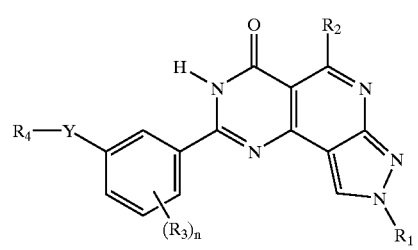

are useful as inhibitors of cGMP PDE especially Type 5.

20 Claims, No Drawings

PYRAZOLOPYRIDOPYRIMIDINE INHIBITORS OF CGMP PHOSPHODIESTERASE

FIELD OF THE INVENTION

The present invention relates to pyrazolopyridopyrimidine compounds, to methods of using such compounds in treating cGMP-associated conditions such as erectile dysfunction, and to pharmaceutical compositions containing such compounds.

BACKGROUND OF THE INVENTION

Erectile dysfunction is the inability to obtain and maintain a penile erection sufficient for sexual intercourse or other sexual expression. A number of factors can place an individual at risk for this disorder, for example, trauma, pelvic surgery, hypercholesterolemia, ischemic heart disease, peripheral vascular disease, chronic renal failure, diabetes, or the use of certain medicaments including some types of antihypertensive agents, digoxin, as well as the excessive use of narcotics, alcohol, tobacco, etc. Methods for treating erectile dysfunction include the use of vacuum devices and penile implants, as well as the administration of medicaments such as yohimbine, papaverine and apomorphine. Improved methods for treating this disorder are sought, however, as the aforementioned methods do not provide sufficient efficacy and/or are accompanied by drawbacks or side effects such as erosion, pain, priapism or gastrointestinal discomfort.

As penile erection is dependent upon the presence of adequate levels of cyclic guanosine 3',5'-monophosphate (cGMP), especially in corpora cavernosa tissue, administration of an inhibitor of a cGMP phosphodiesterase (cGMP PDE) particularly, a selective inhibitor of cGMP PDE Type 5 (PDE 5), provides a means for achieving and maintaining an erection, and therefore for treating erectile dysfunction. See Trigo-Rocha et al., "Nitric Oxide and cGMP: Mediators of Pelvic Nerve-Stimulated Erection in Dogs," *Am. J. Physiol.*, Vol. 264 (February 1993); Bowman et al., "Cyclic GMP Mediates Neurogenic Relaxation in the Bovine Retractor Penis Muscle," *Br. J. Pharmac.*, 81, 665–674 (1984); and Rajfer et al., "Nitric Oxide as a Mediator of Relaxation of the Corpus Cavernosum in Response to Nonadrenergic, Noncholinergic Neurotransmission," *New England J. Med.*, 326, 2, 90–94 (January 1992). Sildenafil, for example, has been described as a PDE 5 inhibitor useful for treating erectile dysfunction. See *Drugs of the Future*, 22, 138–143 (1997).

Recent examples of other compounds claimed as PDE 5 inhibitors include fused pyridazine compounds (WO 96/05176 and U.S. patent application Ser. No. 09/393,833), anthranilic acid derivatives (U.S. Pat. No. 5,716,993), fused pyridopyridazine compounds (U.S. patent application Ser. No. 09/526,162), and quinazolinone compounds (U.S. Pat. No. 6,087,368).

The present invention provides compounds that are potent and selective inhibitors of cGMP PDE 5. These compounds may be employed in treating erectile dysfunction. In view of their activity, these compounds can also be employed in treating other disorders responding to the inhibition of cGMP PDE, such as various cardiovascular disorders.

SUMMARY OF THE INVENTION

The present invention provides pyrazolopyridopyrimidine compounds of the following formula (I) or salts thereof, for use as inhibitors of cGMP PDE, especially Type 5:

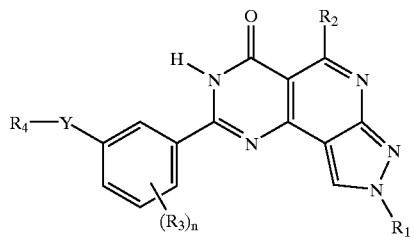

wherein:
  $R_1$ is hydrogen, alkyl or substituted alkyl;
  $R_2$ is hydrogen, halogen, —$OR_5$ or —$NR_5R_6$;
  $R_3$ at each occurrence is selected from hydrogen, halogen, alkyl, substituted alkyl and —$OR_7$;
  $R_4$ is hydrogen, alkyl, substituted alkyl, aryl, heteroaryl or heterocyclo;
  $R_5$, $R_6$ and $R_7$ are independently selected from hydrogen, alkyl and substituted alkyl;
  Y is —$SO_2$— or —(C=O)—; and
  n is 4.

The invention further provides pharmaceutical compositions adapted for use in treating cGMP-associated conditions comprising a pharmaceutically acceptable diluent or carrier and at least one compound of the formula (I) or salt thereof, wherein $R_1$, $R_2$, $R_3$ and $R_4$ are as defined above. The invention further provides methods for treating cGMP-associated conditions comprising administering to a mammal in need of such treatment a therapeutically-effective amount of one or more compounds of the formula (I) or salt thereof, wherein $R_1$, $R_2$, $R_3$ and $R_4$ are as defined above.

DETAILED DESCRIPTION OF THE INVENTION

The following are definitions of terms used in this specification. The initial definition provided for a group or term herein applies to that group or term throughout the present specification, individually or as part of another group, unless otherwise indicated.

The term "alkyl" refers to straight or branched chain hydrocarbon groups having 1 to 12 carbon atoms, preferably 1 to 8 carbon atoms. Lower alkyl groups, that is, alkyl groups of 1 to 4 carbon atoms, are most preferred.

The term "substituted alkyl" refers to an alkyl group as defined above having one, two or three substituents selected from the group consisting of halo, amino, cyano, hydroxy, alkoxy, alkylthio, —NH(alkyl), —NH(cycloalkyl), —N(alkyl)$_2$, carbonyl, carboxy, —$CO_2$-alkyl, cycloalkyl, substituted cycloalkyl, aryl, heteroaryl, or heterocyclo. The term "substituted alkyl" also includes an alkyl group as defined above substituted with N(substituted alkyl) or N(substituted alkyl)$_2$, or in other words, the groups (CH$_2$)$_n$NHR' and (CH$_2$)$_n$NR'R", wherein each of R' and R" comprises a substituted alkyl or form a heterocyclo ring.

The term "alkoxy" refers to an alkyl group as defined above bonded through an oxygen (—O—). The term "alkylthio" refers to an alkyl group as defined above bonded through a sulfur (—S—).

The term "cycloalkyl" refers to fully saturated and partially unsaturated hydrocarbon rings of 3 to 9, preferably 3 to 7, carbon atoms as well as such rings having a fused aryl ring such as indan.

The term "substituted cycloalkyl" refers to such rings having one, two or three substituents, preferably one, selected from the group consisting of alkyl, substituted alkyl, alkoxy, alkylthio, halo, hydroxy, cyano, amino, —NH(alkyl), —NH(cycloalkyl), —N(alkyl)$_2$, carboxy, —CO$_2$-lower alkyl, aryl, heterocyclo, heteroaryl, keto, =N—OH, =N—O-lower alkyl, and a five or six membered ketal, i.e. 1,3-dioxolane or 1,3-dioxane.

The term "halo" refers to chloro, bromo, fluoro and iodo.

The term "aryl" refers to phenyl, 1-naphthyl and 2-naphthyl, with phenyl being preferred. The term "aryl" includes such rings having from zero, one, two or three substituents, selected from the group consisting of alkyl, substituted alkyl, alkoxy, alkylthio, halo, hydroxy, nitro, cyano, amino, —NH(alkyl), —NH(cycloalkyl), —N(alkyl)$_2$, carboxy, —(C=O)alkyl, —CO$_2$-alkyl, cycloalkyl, substituted cycloalkyl, —(C=O)NH$_2$, —(C=O)NH(alkyl), —(C=O)NH(cycloalkyl), —(C=O)N(alkyl)$_2$, —NH—CH$_2$-carboxy, —NH—CH$_2$—CO$_2$-alkyl, phenyl, benzyl, phenylethyl, phenyloxy, phenylthio, heterocyclo, and heteroaryl.

The term "heterocyclo" refers to substituted and unsubstituted non-aromatic 3 to 7 membered monocyclic groups, 7 to 11 membered bicyclic groups, and 10 to 15 membered tricyclic groups which have at least one heteroatom (O, S or N) in at least one of the rings. Each ring of the heterocyclo group containing a heteroatom can contain one or two oxygen or sulfur atoms and/or from one to four nitrogen atoms provided that the total number of heteroatoms in each ring is four or less, and further provided that the ring contains at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Each heterocyclo group may be attached at any available nitrogen or carbon atom. Each heterocyclo group may contain one, two or three substituents selected from the group consisting of halo, amino, cyano, alkyl, substituted alkyl, —NH(alkyl), —NH(cycloalkyl), —N(alkyl)$_2$, alkoxy, alkylthio, hydroxy, nitro, phenyl, benzyl, phenylethyl, phenyloxy, phenylthio, carboxy, —CO$_2$-alkyl, cycloalkyl, substituted cycloalkyl, —(C=O)NH$_2$, —(C=O)NH(alkyl), —(C=O)NH(cycloalkyl), —(C=O)N(alkyl)$_2$, —NH—CH$_2$-carboxy, —NH—CH$_2$—CO$_2$-alkyl, heterocyclo, heteroaryl, keto, =N—OH, =N—O-lower alkyl, and a five or six membered ketal, i.e., 1,3-dioxolane or 1,3-dioxane.

Exemplary monocyclic groups include azetidinyl, pyrrolidinyl, oxetanyl, imidazolinyl, oxazolidinyl, isoxazolinyl, thiazolidinyl, isothiazolidinyl, tetrahydrofuranyl, piperidinyl, piperazinyl, 2-oxopiperazinyl, 2-oxopiperidinyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl.

The term "heteroaryl" refers to substituted and unsubstituted aromatic 5 or 6 membered monocyclic groups, 9 or 10 membered bicyclic groups, and 11 to 14 membered tricyclic groups which have at least one heteroatom (O, S or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain one, two or three substituents selected from the group consisting of halo, amino, cyano, alkyl, substituted alkyl, —NH(alkyl), —NH(cycloalkyl), —N(alkyl)$_2$, alkoxy, alkylthio, hydroxy, nitro, phenyl, benzyl, phenylethyl, phenyloxy, phenylthio, carboxy, —CO$_2$-alkyl, cycloalkyl, substituted cycloalkyl, —(C=O)NH$_2$, —(C=O)NH(alkyl), —(C=O)NH(cycloalkyl), —(C=O)N(alkyl)$_2$, —NH—CH$_2$-carboxy, —NH—CH$_2$-CO$_2$-alkyl, heterocylco, and heteroaryl.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxaxolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridinyl, dihydroisoindolyl, tetrahydroquinolinyl and the like.

Exemplary tricyclic heteroaryl groups include carbazolyl, benzidolyl, phenanthrollinyl, acridinyl, phenanthridinyl, xanthenyl and the like.

Throughout the specification, groups and substituents thereof may be chosen to provide stable moieties and compounds.

The compounds of formula I form salts which are also within the scope of this invention. Reference to a compound of the formula I herein is understood to include reference to salts thereof, unless otherwise indicated.

The term "salt(s)", as employed herein, denotes acidic and/or basic salts formed with inorganic and/or organic acids and bases. In addition, when a compound of formula I contains both a basic moiety, such as, but not limited to an amine or a pyridine or imidazole ring, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds of the formula I may be formed, for example, by reacting a compound of the formula I with an amount of acid or base, such as an equivalent amount, in a medium such as one in which the salt precipitates or in an aqueous medium followed by lyophilization.

The compounds of formula I which contain a basic moiety, such as, but not limited to an amine or a pyridine or imidazole ring, may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The compounds of formula I which contain an acidic moiety, such as, but not limited to a carboxylic acid, may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines [formed with N,N-bis(dehydro-abietyl)ethylenediamine], N-methyl-D-glucamines, N-methyl-D-glucamides, t-butyl amines, and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Prodrugs and solvates of the compounds of this invention are also contemplated herein. The term "prodrug", as employed herein, denotes a compound which, upon administration to a subject, undergoes chemical conversion by metabolic or chemical processes to yield a compound of the formula I, and/or a salt and/or solvate thereof. Solvates of the compounds of formula I are preferably hydrates.

Compounds of the formula I, and salts thereof, may exist in their tautomeric form (for example, as an amide or imino ether). All such tautomeric forms are contemplated herein as part of the present invention.

All stereoisomers of the present compounds, such as those, for example, which may exist due to asymmetric carbons on the $R_2$ to $R_7$ substituents, including enantiomeric forms (which may exist even in the absence of asymmetric carbons) and diastereomeric forms, are contemplated and within the scope of this invention. Individual stereoisomers of the compounds of this invention may, for example, be substantially free of other isomers, or may be admixed, for example, as racemates or with all other or other selected, stereoisomers. The chiral centers of the present invention can have the S or R configuration as defined by the IUPAC 1974 Recommendations.

Methods of Preparation

The compounds of the present invention may be prepared by methods such as those illustrated in the following Schemes. Starting materials are commercially available or can be readily prepared by one of ordinary skill in the art using known methods. For all of the schemes and compounds, the groups $R_1$, $R_2$, $R_3$, and $R_4$ are as described above for a compound of formula I, unless otherwise indicated.

Solvents, temperatures, pressures, and other reaction conditions may readily be selected by one of ordinary skill in the art. For example, in these schemes exemplary hydroxide sources may include sodium hydroxide or lithium hydroxide; an exemplary reducing reagent and inert solvent (for reducing a carboxylic acid or ester group to an alcohol) includes lithium tri-t-butoxyaluminohydride and tetrahydrofuran (THF); exemplary dehydrating/chlorinating agents include $POCl_3$, $PCl_5$, $SOCl_2$ or oxalyl chloride; exemplary leaving groups (LG) include triflate, mesylate, tosylate, or halide; and exemplary reagents (for converting a hydroxyl group to a leaving group) include trifluoromethanesulfonyl chloride, toluenesulfonyl chloride, methanesulfonyl chloride, phosphorus oxychloride, thionyl chloride, and phosphorus pentachloride. Exemplary solvents, as appropriate, may be selected from 1,2-dichlorobenzene, methylene chloride, dimethylformamide (DMF), alcohols, ethers, including diphenyl ether, tetrahydrofuran and dioxane, N,N-dimethylformamide, and acetonitrile, water, mixtures of ethers and water, and the like.

High Speed Analoging (HSA) may be employed in the preparation of compounds.

SCHEME

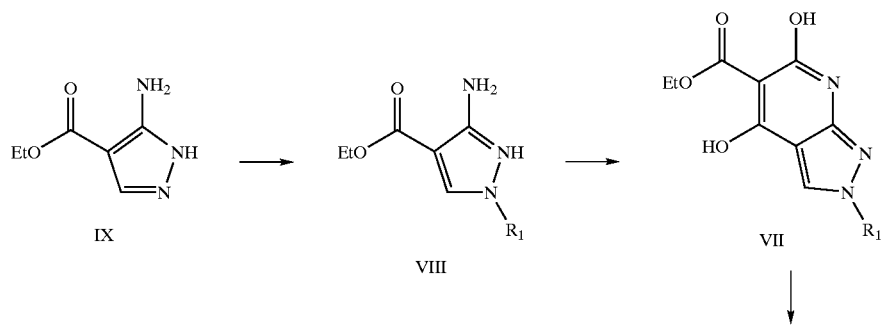

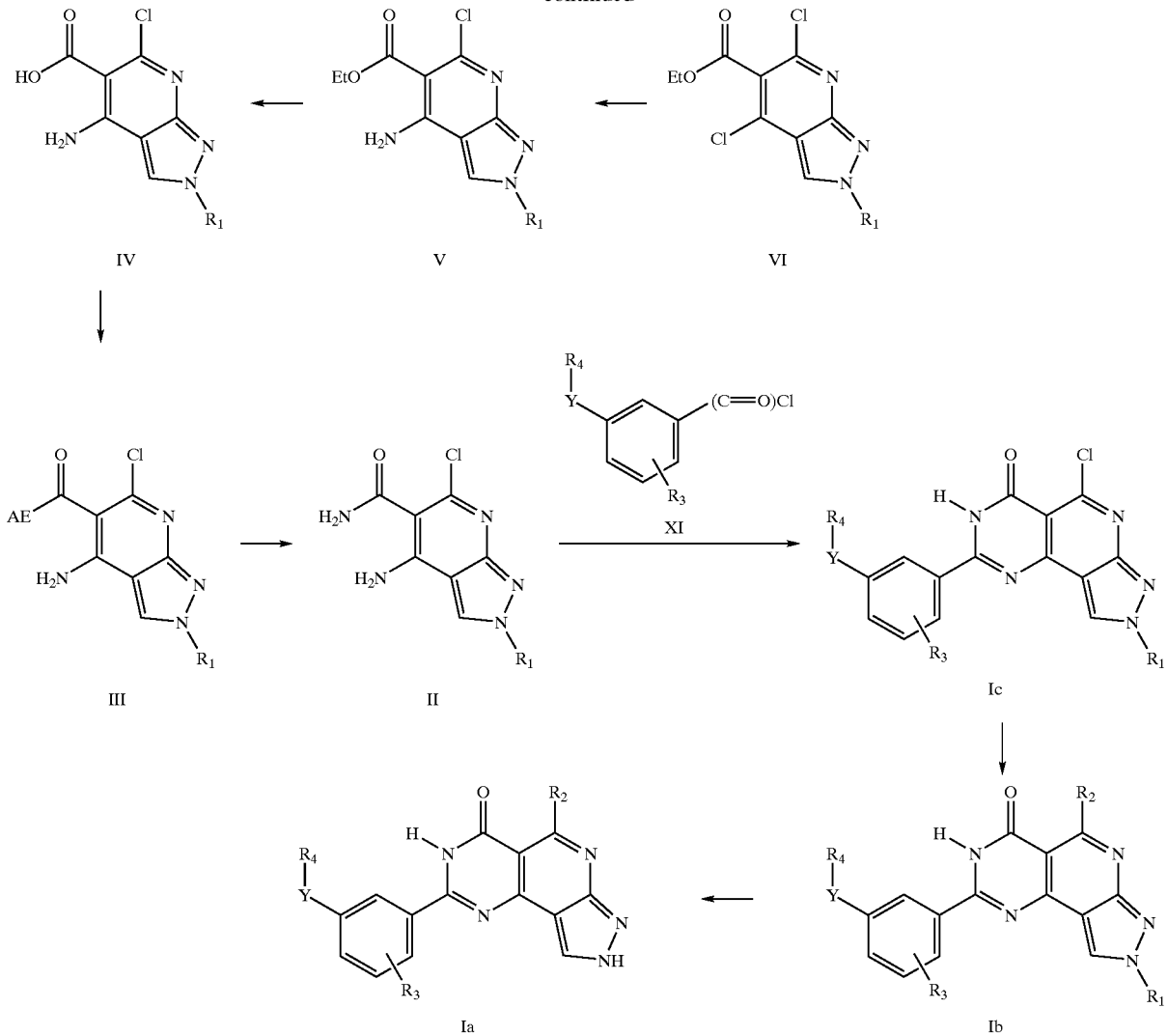

Compounds of formula Ia, wherein $R_1$ is hydrogen, can be prepared from a compound of formula Ib by removal of $R_1$ with an appropriate reagent (e.g., to remove 4-methoxybenzyl group with TFA at an elevated temperature).

Compounds of formula Ib, wherein $R_2$ is hydrogen, can be prepared from a compound of formula Ic by hydrogenation using palladium and hydrogen, for example, in an appropriate solvent, such as MeOH. Compounds of formula Ib, wherein $R_2$ is —$NR_5R_6$, can be prepared from a compound of formula Ic by displacement of the chloride with an appropriate amine ($HNR_5R_6$). The reaction may be performed in a solvent as appropriate, such as an alcohol, in the presence of an appropriate base, such as triethylamine, and typically under elevated temperature. Compounds of formula Ib, wherein $R_2$ is —$OR_5$, can be prepared from a compound of formula Ic by hydrolysis with hydroxides such as NaOH or KOH or alkoxides such as $NaOR_5$ or $KOR_5$ using an appropriate solvent such as $HOR_5$.

Compounds of formula Ic can be prepared from a compound of formula II by first acylation of the amino group with an appropriate benzoyl chloride of formula XI in the presence of a base, such as pyridine, followed by treatment with an appropriate base, such as potassium tert-butoxide, to effect cyclization. The reaction typically is carried out in a solvent as appropriate, such as an alcohol, under elevated temperature.

Compounds of formula II can be prepared via the aminolysis of an active ester (AE) of formula III using ammonia in an inert solvent, such as THF.

Compounds of formula III can be prepared via activation of the carboxylic acid in compounds of formula IV using an appropriate carboxylic acid activating agent in an appropriate solvent. Exemplary activating agents include pentafluorophenol and carbonyldiimidazole.

Compounds of formula IV can be prepared by the hydrolysis of compounds of formula V using a hydroxide source and appropriate solvent (e.g., water, alcohols, and a mixture of ether and water).

Compounds of formula V can be prepared via the selective aminolysis of a compound of formula VI using ammonia in an inert solvent, such as THF.

Compounds of formula VI can be prepared by reacting compounds of formula VII with an appropriate dehydrating/chlorinating agent, typically under elevated temperatures.

Compounds of formula VII can be prepared from compounds of formula VII by a condensation with a malonate derivative using base in an appropriate solvent. Sodium alkoxides are exemplary bases and alcohols exemplary solvents.

Compounds of formula VIII can be prepared by reacting compound of formula IX with an alkylating agent under basic conditions in an inert solvent.

Compound of formula IX is commercially available. Compounds of formula XI are either commercially available or available via methods known to one skilled in the art.

Preferred Compounds

Preferred compounds of this invention are those of formula (I) and/or pharmaceutically acceptable salts thereof having the following definitions:

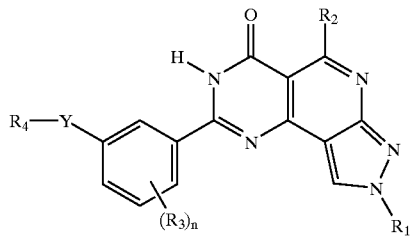

I wherein:
$R_1$ is hydrogen or substituted alkyl;
$R_2$ is hydrogen, halogen, —$OR_5$ or —$NR_5R_6$;
$R_3$ at each occurrence is selected from hydrogen or —$OR_7$;
$R_4$ is aryl, heteroaryl or heterocyclo;
$R_5$, $R_6$ and $R_7$ are independently selected from hydrogen, alkyl and substituted alkyl;
Y is —$SO_2$— or —(C=O)—; and
n is 4.

More preferred are the compounds of formula (I), above, and pharmaceutically acceptable salts thereof, wherein
$R_1$ is hydrogen or —$CH_2$-aryl;
$R_2$ is hydrogen, halogen, or —$NHR_6$;
$R_3$ at one occurrence is —O-alkyl and at each other occurrence is hydrogen;
$R_4$ is heterocyclo;
$R_6$ is substituted alkyl;
Y is —$SO_2$—; and
n is 4.

Most preferred are the compounds of formula (I) and/or pharmaceutically acceptable salts thereof, wherein:
$R_1$ is hydrogen or —$CH_2$-aryl;
$R_2$ is hydrogen, halogen, or —NH—$CH_2$-aryl;
$R_3$ at one occurrence is —$OCH_2CH_3$ or —$OCH_2CH_2CH_3$ and at each other occurrence is hydrogen;
$R_4$ is optionally-substituted piperazinyl or pyrrolidinyl;
Y is —$SO_2$—; and
n is 4.

Utility

The compounds and compositions of this invention inhibit cGMP PDE, and in particular are potent and selective inhibitors of cGMP PDE 5. Thus, these compounds and compositions are useful in treating cGMP-associated conditions. A "cGMP-associated condition", as used herein, denotes a disorder which can be treated by inhibiting cGMP PDE or elevating the level of cGMP in a subject, wherein treatment comprises prevention, partial alleviation, or cure of the disorder. Inhibition of cGMP PDE or elevation of the cGMP level may occur locally, for example, within certain tissues of the subject, or more extensively throughout the subject being treated for such a disorder. Treatment may be facilitated wherein elevation of the cGMP level potentiates additional beneficial therapeutic effects, such as where elevation of the cGMP level potentiates the effects of endothelium-derived relaxing factor.

The inventive compounds and compositions are useful for treating a variety of cardiovascular diseases including, but not limited to, hypertension, angina (stable, unstable, and variant), (congestive) heart failure, restenosis, atherosclerosis, and dyslipidemia, as well as reduced blood vessel patency, thrombus, both venous and arterial, myocardial infarction, peripheral vascular disease, stroke, bronchitis, chronic asthma, allergic asthma, allergic rhinitis, glaucoma, benign prostate hyperplasia (BPH),and forms of cancer responsive to the inhibition of cGMP PDE. In addition, these compounds are useful in treating sexual dysfunction in both men (erectile dysfunction, for example, due to diabetes mellitus, spinal cord injury, radical prostatectomy, psychogenic etiology or any other cause) and women by improving blood flow to the genitalia, especially, the corpus cavernosum. The compounds and compositions of this invention also are useful in treating diabetes mellitus and related conditions, and diseases of the gastrointestinal tract, such as those characterized by disorders of gut motility, including gastric paresis.

The present invention thus provides methods for treating cGMP-associated conditions, comprising administering to a subject in need thereof an effective amount of at least one compound of the formula I or a salt thereof, and/or pharmaceutical compositions as described above. Other therapeutic agents such as those described below may be employed in combination with the compounds of formula I. In the methods of the present invention, such other therapeutic agent(s) may be administered prior to, simultaneously with, or following the administration of the inventive compound(s) and compositions.

The present invention also provides pharmaceutical compositions capable of treating a cGMP-associated condition, as described above. The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds and compositions of formula I may be administered by any suitable means, for example, orally, such as in the form of tablets, capsules, granules or powders; sublingually; bucally; parenterally, such as by subcutaneous, intravenous, intramuscular or intrasternal injection or infusion techniques (e.g., as sterile injectable aqueous or non-aqueous solutions or suspensions); nasally such as by inhalation spray; topically, such as in the form of a cream or ointment; rectally such as in the form of suppositories; or liposomally; in dosage unit formulations containing non-toxic, pharmaceutically acceptable vehicles or diluents. These compounds may, for example, be administered in a form suitable for immediate release or extended release. Immediate release or extended release may be achieved by the use of suitable pharmaceutical compositions or, particularly in the case of extended release, by the use of devices such as subcutaneous implants or osmotic pumps.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The compounds of formula I may also be delivered through the oral cavity by sublingual and/or buccal administration. Molded tablets, compressed tablets or freeze-dried tablets are exemplary forms that may be used. Exemplary compositions include those formulating the inventive compound(s) with fast-dissolving diluents such as mannitol, lactose, sucrose, and/or cyclodextrins. Also included in such formulations may be high molecular weight excipients such as celluloses (AVICEL®) or polyethylene glycols (PEG). Such formulations may also include an excipient to aid mucosal adhesion such as hydroxypropyl cellulose (HPC), hydroxypropyl methyl cellulose (HPMC), sodium carboxymethyl cellulose (SCMC), maleic anhydride copolymer (e.g., GANTREZ®), and agents to control release such as polyacrylic copolymer (e.g., CARBOPOL 934®). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

Exemplary compositions for topical administration include a topical carrier such as PLASTIBASE® (mineral oil gelled with polyethylene).

The effective amount of a compound of the present invention may be determined by one of ordinary skill in the art, and includes exemplary dosage amounts for an adult human of from about 0.05 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like, subject to cGMP-associated conditions.

The inventive compounds and compositions may be employed alone or in combination with each other and/or other suitable therapeutic agents useful in treating cGMP-associated conditions such as other cGMP PDE inhibitors, particularly other cGMP PDE 5 inhibitors, modulators of the large-conductance calcium-activated potassium (BK) channels, prostanoids, α-adrenergic agonists, endothelin antagonists, angiotensin II (especially, subtype $AT_1$) antagonists, angiotensin converting enzyme (ACE) inhibitors, renin inhibitors, and serotonin ($5-HT_{2C}$) agonists.

Exemplary of such other therapeutic agents are the following: phentolamine, yohimbine, papaverine, apomorphine, sildenafil, pyrazolopyrimidinones as described in U.S. Pat. Nos. 5,272,147; 5,250,534; 5,426,107; and 5,346,901, quinazolinones as described in U.S. Pat. No. 5,482,941; $AT_1$ antagonists such as from losartan, irbesartan, valsartan, and candesartan; $ET_A$ antagonists such as bosentan, ABT-627, and those described in U.S. Pat. No. 5,612,359 and U.S. patent application Ser. No. 60/035,832, filed Jan. 30, 1997; PDE 5 inhibitors selected from imidazoquinazolines (see WO 98/08848), carbazoles (see WO 97/03675, WO 97/03985 and WO 95/19978), imidazopurinones (see WO 97/19947), benzimidazoles (see WO 97/24334), pyrazoloquinolines (see U.S. Pat. No. 5,488,055), quinazolinones as described in U.S. Pat. No. 6,087,368, pyridines as described in U.S. patent application Ser. No. 60/100,655 filed Sep. 16, 1998, anthranilic acid derivatives (see WO 95/18097), fused heterocycles (see WO 98/07430) and thienopyrimidines (see DE 19632423); and $5-HT_{2C}$ agonists selected from indoles (see *J. Med. Chem.,* 40, 2762–2769 [1997], EP 655440 and EP 657426), and modulators of the large-conductance calcium-activated potassium (BK) channels as described in U.S. Pat. Nos. 5,565,483 and 5,602,169, and in WO 98/04135 and WO98/23273.

The above other therapeutic agents, when employed in combination with the compounds of the present invention, may be used, for example, in those amounts indicated in the Physicians' Desk Reference (PDR) or as otherwise determined by one of ordinary skill in the art.

The following assay can be employed in ascertaining the degree of activity of a compound as a cGMP PDE inhibitor. Compounds described in the following Examples have been tested in this assay, and have shown activity.

PDE Scintillation Proximity Assay Protocol

Sonicated human platelet homogenates are prepared by the method of Seiler, et al. (Seiler, S., Gillespie, E., Arnold, A. J., Brassard, C. L., Meanwell, N. A. and Fleming, J. S., "Imidazoquinoline Derivatives: Potent Inhibitors of Platelet Camp Phosphodiesterase which Elevate Camp Levels and Activate Protein Kinase in Platelets," *Thrombosis Research,* 62: 31–42 (1991)). PDE 5 is abundant in human platelets, and accounts for approximately 90% of the cGMP hydrolytic activity in the homogenates. When necessary, PDE 5 can be resolved from other PDE activities in the homogenates by anion exchange chromatography on a fast protein liquid chromatography system (FPLC) using a Mono-Q anion exchange column (Pharmacia) eluted with a linear gradient of 10 mM–450 mM NaCl.

The phosphodiesterase activity is assayed using a commercially available phosphodiesterase [$^3$H]cGMP scintillation proximity (SPA) assay kit (Amersham). The manufacturer's protocol is followed explicitly except that the reactions are carried out at RT and 3 mM nonradioactive cGMP is included in the suspension of SPA beads to prevent the synthesis of any additional radioactive products.

The conditions used to determine HPLC (LC) retention times for the Preparations and Examples were as follows: a Shimadzu LC-10AS, YMC S5 ODS 4.6×50 mm ballistic column was used, using a flow rate of 4 mL/min with a linear eluent gradient over 4 minutes with detection done at a wavelength of 220 nm. Two different eluent gradients were used. Gradient 1 was 0% B/100% A to 100% B/0% A. Gradient 2 was 40% B/60% A to 80% B/20% A. Solvent mixture A=10% MeOH/90% $H_2O$/0.1% TFA, and solvent mixture B=90% MeOH/10% $H_2O$/0.1% TFA. In the Examples, these conditions are referred to as "Gradient 1" and "Gradient 2."

All documents cited in the present specification are incorporated herein by reference in their entirety.

The following Examples illustrate embodiments of the inventive compounds and starting materials, and are not intended to limit the scope of the claims. For ease of reference, the following abbreviations are used in the Examples, below:

Abbreviations

DMSO=dimethylsulfoxide
HPLC=high pressure liquid chromatography
LRMS=low resolution mass spectrometry
mp=melting point
tlc=thin layer chromatography
RT=room temperature
h=hour(s)
Ac=acetyl
DCC=dicyclohexyl carbodiimide
DCM=dichloromethane
DMF=dimethyl formamide
Et=ethyl
Me=methyl
MeOH=methanol
HOAc=acetate
EtOAc=ethyl acetate
EDAC.HCl=ethyl-3-(dimethylamino)propyl carbodiimide, hydrochloride salt
HOBT=hydroxybenztriazole
NMP=N-methyl pyrrolidinone
TEA=triethylamine
THF=tetrahydrofuran

PREPARATION OF STARTING MATERIALS

Preparation 1

5-Amino-2-p-methoxybenzyl-4-pyrazolecarboxylic acid ethyl ester

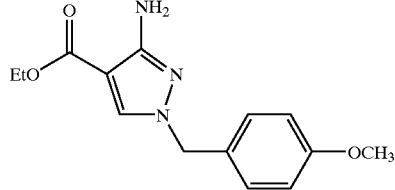

To a solution of 3-amino4-carbethoxypyrazole (15 g, 96.7 mmol) in acetonitrile (750 mL) was add NaH (60% oil dispersion, 4 g, 100 mmol) at rt. After 15 min., 4-methoxybenzyl chloride (15.7 g, 100 mmol) was added with stirring. The reaction was allowed to run for 24 h. The reaction mixture was then diluted with EtOAc and washed with H$_2$O, brine and dried (Na$_2$SO$_4$). Removal of the solvent gave the crude product which was further purified by flash column (silica gel, EtOAc/hexane, 1:1) to give ethyl 5-amino-2-p-methoxybenzyl-4-pyrazolecarboxylate (4.2 g, LC: 3.10' MH$^+$: 276) along with Ethyl 5-amino-1-p-methoxybenzyl-4-pyrazolecarboxylate (4.5 g) (LC: 3.07' [Gradient 1] MH$^+$: 276) and mixture of the two (10.2 g).

Preparation 2

4,6-Dihydroxy-2-(4-methoxyphenyl)methyl-2H-pyrazolo[3,4-b]pyridine-5-carboxylic acid ethyl ester

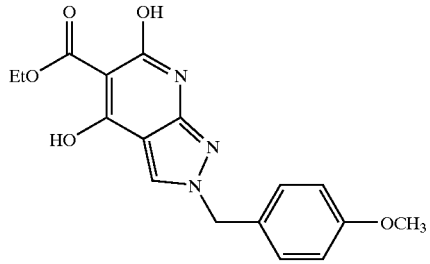

To a solution of diethyl malonate (9.6 g, 60 mmol) in a freshly prepared solution of NaOEt in EtOH (from 2.52 g of 60% oil dispersion NaH and 40 mL of EtOH) was added a solution of 5-amino-2-p-methoxybenzyl4-pyrazolecarboxylic ethyl ester (4.2 g, 15 mmol) in EtOH (60 mL) at rt. The resulting solution was refluxed for 20 h. The mixture was concentrated and the residue was dissolved in H$_2$O (250 mL) and washed with EtOAc (60 mL). The aqueous layer was acidified with AcOH to pH 5. The product (5.1 g) was collected by filtration and dried under high vacuum. LC: 3.47' (Gradient 1); MH$^+$: 344

Preparation 3

4,6-Dichloro-2-(4-methoxyphenyl)methyl-2H-pyrazolo[3,4-b]pyridine-5-carboxylic acid ethyl ester

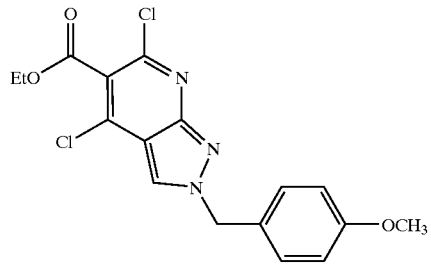

A suspension of 4,6-dihydroxy-2-(4-methoxyphenyl) methyl-2H-pyrazolo[3,4-b]pyridine-5-carboxylic acid ethyl ester (5 g) in POCl$_3$ (40 mL) was refluxed under nitrogen with stirring for 2 h. The POCl$_3$ was removed and the residue was codistilled with EtOAc. The residue was subjected to flash column (silica gel, EtOAc/hexane, 3:7) to give 1.28 g of the above product. LC:4.41' (Gradient 1) MH$^+$:380.

Preparation 4

4-Amino-6-chloro-2-(4-methoxyphenyl)methyl-2H-pyrazolo[3,4-b]pyridine-5-carboxylic acid ethyl ester

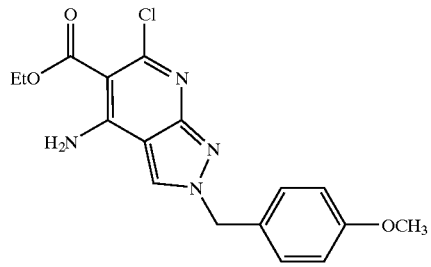

A solution of 4,6-dichloro-2-(4-methoxyphenyl)methyl-2H-pyrazolo[3,4-b]pyridine-5-carboxylic acid ethyl ester (1.21 g) in EtOH/THF was saturated with NH$_3$. Then solution was then stirred for 12 days (the solution was resaturated several times during that time). The solvent was removed and the residue was dissolved in EtOAc (250 mL). The solution was washed with aqueous NaCHCO$_3$ and dried. Removal of the solvent gave the product (1 g) as a white solid. LC: 3.84 (Gradient 1); MH$^+$: 347.

Preparation 5

4-Amino-6-chloro-2-(4-methoxyphenyl)methyl-2H-pyrazolo[3,4-b]pyridine-5-carboxylic acid

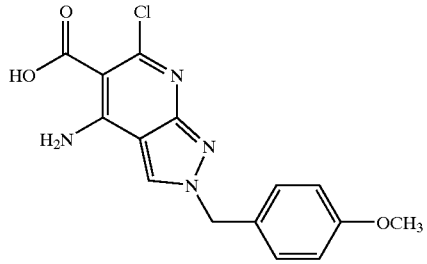

A solution of 4-amino-6-chloro-2-(4-methoxyphenyl)methyl-2H-pyrazolo[3,4-b]pyridine-5-carboxylic acid ethyl ester (800 mg) in NaOH (1N)/MeOH/THF (1:1:1, 15 mL) was stirred for 4 days. The acidity of the reaction mixture was adjusted to pH 5–6 with AcOH. The THF and MeOH were removed. The residue was dissolved in water (30 mL) then extracted with EtOAc (3×100 mL). The combined extracts were dried (NaSO$_4$). Removal of the solvent gave the desired product (746 mg) as white solid. LC: 3.13 (Gradient 1), MH$^+$: 333

Preparation 6

4-Amino-6-chloro-2-(4-methoxyphenyl)methyl-2H-pyrazolo[3,4-b]pyridine-5-carboxylic acid pentafluorophenyl ester

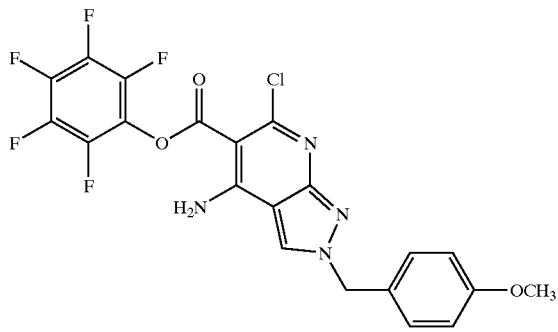

To a cold (0° C.) solution of 4-amino-6-chloro-2-(4-methoxyphenyl)methyl-2H-pyrazolo[3,4-b]pyridine-5-carboxylic acid (952 mg, 2.86 mmol) and pentafluorophenol (830 mg) in DMF was added a solution of DCC (620 mg, 3 mmol) in EtOAc (9 mL). After work up the crude product was purified by flash column (silica gel, EtOAc/hexane, 1:1) to give the desired product (1.27 g) as a white solid. LC: 4.64 (Gradient 1), MH$^+$: 499.

Preparation 7

4-Amino-6-chloro-2-(4-methoxyphenyl)methyl-2H-pyrazolo[3,4-b]pyridine-5-carboxamide

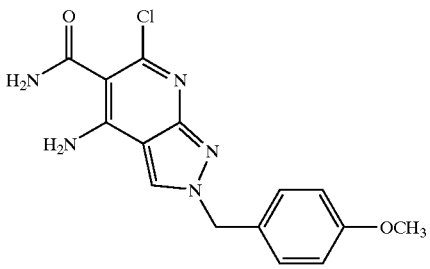

A solution of 4-amino-6-chloro-2-(4-methoxyphenyl)methyl-2H-pyrazolo[3,4-b]pyridine-5-carboxylic acid pentafluorophenyl ester (374 mg) in anhydrous THF was saturated with NH$_3$ gas and stirred overnight. Removal of the solvent gave the desired product as a white solid (contain some pentafluorophenol). LC: 2.60 (Gradient 1); MH$^+$: 332.

Example 1

(3R)-1-[[3-(5-Chloro-4,8-dihydro-8-[(4-methoxyphenyl)methyl]-4-oxo-1H-pyrazolo[4',3':5,6]pyrido[4,3-d]pyrimidin-2-yl)-4-propoxyphenyl]sulfonyl]-3-(dimethylamino)pyrrolidine

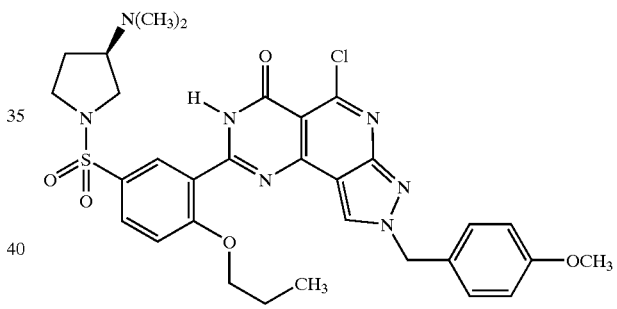

To a solution of 5-[(3R)-(+)-3-dimethylaminopyrrolidinyl)sulfonyl]-2-propoxybenzoic acid (240 mg, 0.66 mmol) in dry DCM (5 mL) was added a solution of oxalyl chloride in DCM (2M, 1.32 mL, 2.65 mmol) and several drops of DMF under nitrogen. After complete conversion to acyl chloride, the mixture was concentrated and pumped dried. Then it was dissolved in THF (3 mL). This solution was then added dropwise to a stirring mixture of 4-amino-6-chloro-2-(4-methoxyphenyl)methyl-2H-pyrazolo[3,4-b]pyridine-5-carboxamide (212 mg, 0.64 mmol) and potassium bis(trimethylsilyl)amide (383 mg, 1.92 mmol) in dry THF (5 mL) under nitrogen. The reaction was continued for 3 h. The solvent was removed and dissolved in EtOAc (120 mL), then washed with saturated NaHCO$_3$ (2×20 mL) and dried (Na$_2$SO$_4$). Removal of the solvent gave a mixture of cyclized and uncyclized products.

To a solution of the above product (220 mg) in t-BuOH (9 mL) was added 4A molecular sieves (307 mg) and a solution of potassium tert-butoxide in t-BuOH (1 M, 360 μL). The mixture was then heated at reflux for 2 h. After cooling to rt, the reaction was quenched with AcOH (25 μL) and concentrated. The residue was suspended in EtOAc/ether (1:1) and filtered through a thin celite pad and washed with EtOAc/ether (1:1). The combined filtrate was concentrated to give the crude product. Further purification by flash column (silica gel, 5% MeOH in dichloromethane) gave the desired product (93 mg). LC: 3.64 (Gradient 2), MH$^+$: 652.

Example 2

1-[[3-[5-Chloro-4,8-dihydro-8-[(4-methoxyphenyl)methyl]-4-oxo-1H-pyrazolo[4',3':5,6]pyrido[4,3-d]pyrimidin-2-yl]-4-ethoxyphenyl]sulfonyl]-4-methylpiperazine

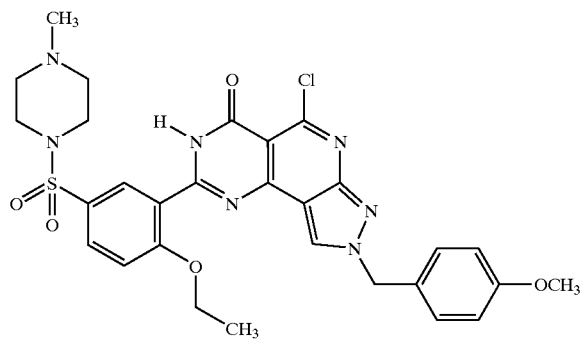

Example 2 was prepared according to the procedure for example 1, using 5-[(4-methylpiperazinyl)sulfonyl]-2-ethoxybenzoic acid instead of 5-[(3R)-(+)-3-dimethylaminopyrrolidinyl)sulfonyl]-2-propoxybenzoic acid. LC:4.14' (Gradient 1); MH$^+$: 624.

Example 3

1-[[3-[5-Chloro-4,8-dihydro-8-[(4-methoxyphenyl)methyl]-4-oxo-1H-pyrazolo[4',3':5,6]pyrido[4,3-d]pyrimidin-2-yl]-4-propoxyphenyl]sulfonyl]-4-ethylpiperazine

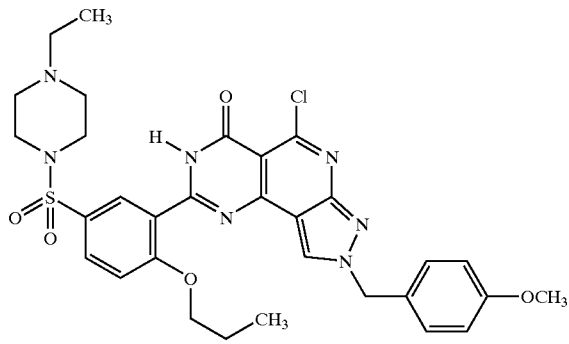

Example 3 was prepared according to the procedure for example 1, using 5-[(4-ethylpiperazinyl)sulfonyl]-2-propoxybenzoic acid instead of 5-[(3R)-(+)-3-dimethylaminopyrrolidinyl)sulfonyl]-2-propoxybenzoic acid. LC: 3.62 (Gradient 2); MH$^+$: 652.

Example 4

1-[[3-[4,8-Dihydro-5-hydroxy-8-[(4-methoxyphenyl)methyl]-4-oxo-1H-pyrazolo[4',3':5,6]pyrido[4,3-d]pyrimidin-2-yl]-4-propoxyphenyl]sulfonyl]-4-ethylpiperazine

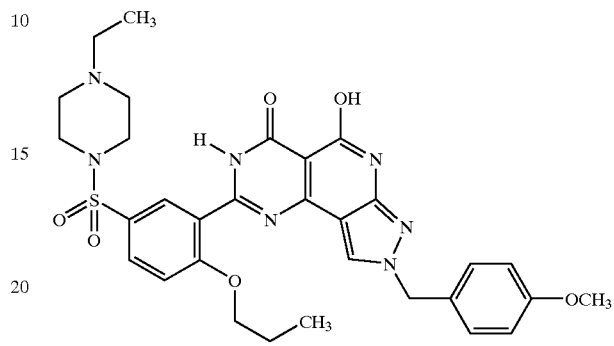

To the uncyclized intermediate from example 3 (30 mg) under nitrogen was added K—OtBu (1M, 0.05 mL) and HOtBu (2 mL). The mixture was then heated at 95° C. for 1 h. After cooling to rt, the mixture was subjected to preparative HPLC to give the titled compound (4.5 mg). LC: 3.54' (Gradient 1); MH$^+$: 634.

Example 5

1-[[3-(4,8-Dihydro-5-hydroxy-4-oxo-1H-pyrazolo[4',3':5,6]pyrido[4,3-d]pyrimidin-2-yl)-4-propoxyphenyl]sulfonyl]-4-ethylpiperazine

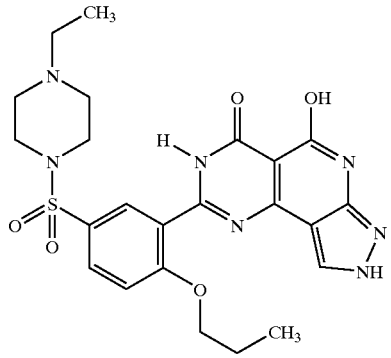

A solution of 1-[[3-[5-Chloro-4,8-dihydro-8-[(4-methoxyphenyl)methyl]-4-oxo-1H-pyrazolo[4',3':5,6]pyrido[4,3-d]pyrimidin-2-yl]-4-propoxyphenyl]sulfonyl]-4-ethylpiperazine (20 mg) in TFA (8 mL) was heated at 70° C. under nitrogen for 2 h. After cooling to rt, the mixture was subjected to preparative HPLC to give the titled compound (15 mg). LC:2.65' (Gradient 1); MH$^+$: 514.

Example 6

(3R)-3-(Dimethylamino)-1-[[3-(4,8-dihydro-4-oxo-1H-pyrazolo[4',3':5,6]pyrido[4,3-d]pyrimidin-2-yl)-4-propoxyphenyl]sulfonyl]pyrrolidine

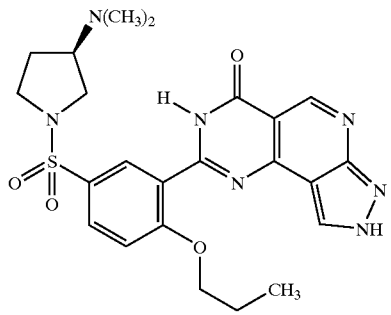

A mixture of (3R)-1-[[3-(5-Chloro-4,8-dihydro-8-[(4-methoxyphenyl)methyl]-4-oxo-1H-pyrazolo[4',3':5,6]pyrido[4,3-d]pyrimidin-2-yl)-4-propoxyphenyl]sulfonyl]-3-(dimethylamino)pyrrolidine (18 mg) and Pd/C (10%, 19 mg) in 10% TEA/MeOH (1 mL) was stirred under H$_2$ overnight. The reaction mixture was filtered through celite and then a 0.45 micron nylon filter. The filtrate was concentrated to give the deschloro compound (16 mg). This compound was dissolved in TFA (2 mL) and heated with stirring at 60° C. for one hour. TFA was removed in vacuo and the residue purified by preparative HPLC to give the titled compound as a TFA salt (7.6 mg). LC: 0.96' (Gradient 2); MH$^+$: 498.

Example 7

(3R)-3-(Dimethylamino)-1-[[3-[5-[[(3-chloro-4-methoxyphenyl)methyl]-amino]-4,8-dihydro-8-[(4-methoxyphenyl)methyl]-4-oxo-1H-pyrazolo[4',3':5,6]pyrido[4,3-d]pyrimidin-2-yl]-4-propoxyphenyl]sulfonyl]pyrrolidine

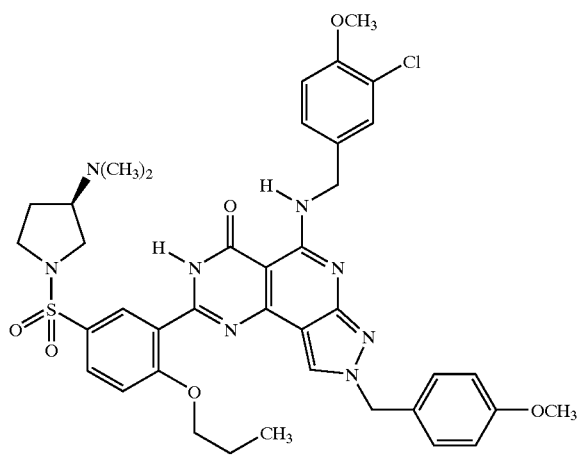

A mixture of (3R)-1-[[3-(5-Chloro-4,8-dihydro-8-[(4-methoxyphenyl)methyl]-4-oxo-1H-pyrazolo[4',3':5,6]pyrido[4,3-d]pyrimidin-2-yl)-4-propoxyphenyl]sulfonyl]-3-(dimethylamino)pyrrolidine (39 mg, 0.06 mmol), 3-chloro-4-methoxybenzylamine.HCl (25 mg, 0.12 mmol) and DIEA (78 mg, 0.6 mmol) in n-BuOH was heated at 125° C. under nitrogen for 4 h. The reaction mixture was concentrated and the residue was chromatographed (silica gel, 5% MeOH in DCM) to give the desired product (42.6 mg) as a yellow solid. LC: 4.36' (Gradient 1); MH$^+$: 787.

Example 8

(3R)-3-(Dimethylamino)-1-[[3-[5-[[(4-fluorophenyl)methyl]amino]-4,8-dihydro-8-[(4-methoxyphenyl)methyl]-4-oxo-1H-pyrazolo[4',3':5,6]pyrido[4,3-d]pyrimidin-2-yl]-4-propoxyphenyl]sulfonyl]pyrrolidine

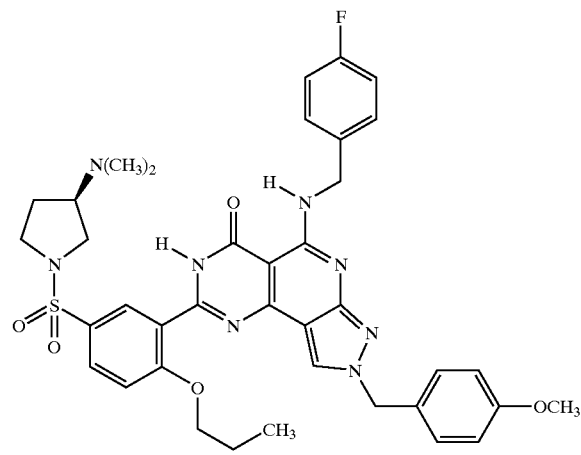

Example 8 was prepared by same method as example 7, using 4-fluorobenzylamine instead of 3-chloro-4-methoxybenzylamine. LC:4.36' (Gradient 1), MH$^+$:741.

Example 9

(3R)-1-[[3-[5-[[(3-Chloro-4-methoxyphenyl)methyl]amino]-4,8-dihydro-4-oxo-1H-pyrazolo[4',3':5,6]pyrido[4,3-d]pyrimidin-2-yl]-4-propoxyphenyl]sulfonyl]-3-(dimethylamino)pyrrolidine

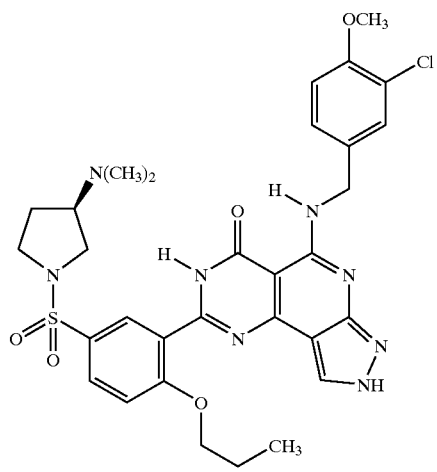

A solution of (3R)-3-(Dimethylamino)-1-[[3-[5-[[(3-chloro-4-methoxyphenyl)methyl]amino]-4,8-dihydro-8-[(4-methoxyphenyl)methyl]-4-oxo-1H-pyrazolo[4',3':5,6]pyrido[4,3-d]pyrimidin-2-yl]-4-propoxyphenyl]sulfonyl]pyrrolidine in TFA (4 mL) was heated at reflux for 1 h. under nitrogen. After removal of the excess TFA, the residue was purified by preparative HPLC to give the desired product (32 mg) as a TFA salt. LC: 3.12 (Gradient 2); MH$^+$: 667.

Example 10

(3R)-3-(Dimethylamino)-1-[[3-[5-[[(4-fluorophenyl)methyl]amino]-4,8-dihydro-4-oxo-1H-pyrazolo[4',3':5,6]pyrido[4,3-d]pyrimidin-2-yl]-4-propoxyphenyl]sulfonyl]pyrrolidine

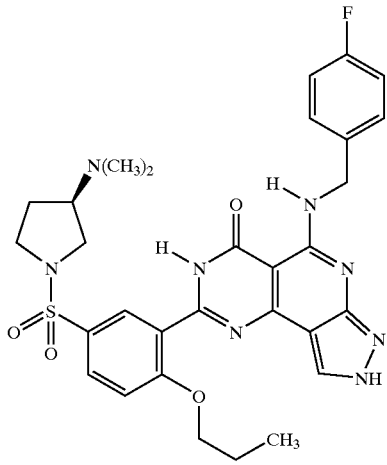

Example 10 was prepared by same method as example 9, starting with example 8. LC:2.95' (Gradient 2); MH+:621.

What is claimed is:

1. A compound of the formula (I) or a pharmaceutically-acceptable salt thereof:

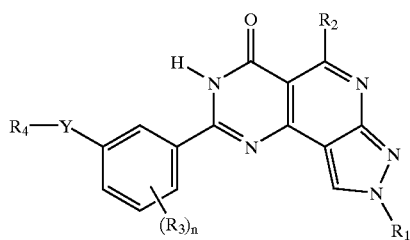

wherein:

$R_1$ is hydrogen, alkyl or substituted alkyl;
$R_2$ is hydrogen, halogen, —$OR_5$ or —$NR_5R_6$;
$R_3$ at each occurrence is selected from hydrogen, halogen, alkyl, substituted alkyl and —$OR_7$;
$R_4$ is hydrogen, alkyl, substituted alkyl, aryl, heteroaryl or heterocyclo, provided, however, that $R_4$ is not hydrogen when Y is —$SO_2$—;
$R_5$, $R_6$ and $R_7$ are independently selected from hydrogen, alkyl and substituted alkyl;
Y is —$SO_2$— or —(C=O)— provided, however, that Y is not —$SO_2$— when $R_4$ is hydrogen; and
n is 4.

2. The compound of claim 1 or a pharmaceutically-acceptable salt thereof, wherein:

$R_1$ is hydrogen or substituted alkyl;
$R_3$ at each occurrence is hydrogen or —$OR_7$; and
$R_4$ is aryl, heteroaryl or heterocyclo.

3. The compound of claim 1 or a pharmaceutically-acceptable salt thereof, wherein:

$R_1$ is hydrogen or —$CH_2$-aryl;
$R_2$ is hydrogen, halogen, or —$NHR_6$;

$R_3$ at one occurrence is —O-alkyl and at each other occurrence is hydrogen;
$R_4$ is heterocyclo;
$R_6$ is substituted alkyl; and
Y is —$SO_2$—.

4. The compound of claim 1 or a pharmaceutically-acceptable salt thereof, wherein.

$R_1$ is hydrogen or —$CH_2$-aryl;
$R_2$ is hydrogen, halogen, or —NH—$CH_2$-aryl;
$R_3$ at one occurrence is —$OCH_2CH_3$ or —$OCH_2CH_2CH_3$ and at each other occurrence is hydrogen;
$R_4$ is optionally-substituted piperazinyl or pyrrolidinyl; and
Y is —$SO_2$—.

5. The compound of claim 1 or a pharmaceutically-acceptable salt thereof, wherein $R_4$ is heterocyclo.

6. The compound of claim 5 or a pharmaceutically-acceptable salt thereof, wherein $R_4$ is piperazinyl or pyrrolidinyl optionally-substituted with alkyl, $NH_2$, NH(alkyl), or N(alkyl)$_2$.

7. The compound of claim 1 or a pharmaceutically-acceptable salt thereof, wherein $R_1$ is hydrogen.

8. The compound of claim 7 or a pharmaceutically-acceptable salt thereof, wherein $R_2$ is hydrogen or halogen.

9. The compound of claim 1 or a pharmaceutically-acceptable salt thereof, wherein $R_3$ at one occurrence is —$OCH_2CH_3$ or —$OCH_2CH_2CH_3$ and at each other occurrence is hydrogen.

10. The compound of claim 9, wherein Y is —$SO_2$—.

11. The compound of claim 1 selected from:

(3R)-1-[[3-(5-chloro-4,8-dihydro-8-[(4-methoxyphenyl)methyl]-4-oxo-1H-pyrazolo[4',3':5,6]pyrido[4,3-d]pyrimidin-2-yl)-4-propoxyphenyl]sulfonyl]-3-(dimethylamino)pyrrolidine;

1-[[3-[5-chloro-4,8-dihydro-8-[(4-methoxyphenyl)methyl]-4-oxo-1H-pyrazolo[4',3':5,6]pyrido[4,3-d]pyrimidin-2-yl]-4-ethoxyphenyl]sulfonyl]-4-methylpiperazine;

1-[[3-[5-chloro-4,8-dihydro-8-[(4-methoxyphenyl)methyl]-4-oxo-1H-pyrazolo[4',3':5,6]pyrido[4,3-d]pyrimidin-2-yl]-4-propoxyphenyl]sulfonyl]-4-ethylpiperazine;

1-[[3-[4,8-dihydro-5-hydroxy-8-[(4-methoxyphenyl)methyl]-4-oxo-1H-pyrazolo[4',3':5,6]pyrido[4,3-d]pyrimidin-2-yl]-4-propoxyphenyl]sulfonyl]-4-ethylpiperazine;

1-[[3-(4,8-dihydro-5-hydroxy-4-oxo-1H-pyrazolo[4',3':5,6]pyrido[4,3-d]pyrimidin-2-yl)-4-propoxyphenyl]sulfonyl]-4-ethylpiperazine;

(3R)-3-(dimethylamino)-1-[[3-(4,8-dihydro-4-oxo-1H-pyrazolo[4',3':5,6]pyrido[4,3-d]pyrimidin-2-yl)-4-propoxyphenyl]sulfonyl]pyrrolidine;

(3R)-3-(dimethylamino)-1-[[3-[5-[[(3-chloro-4-methoxyphenyl)methyl]amino]-4,8-dihydro-8-[(4-methoxyphenyl)methyl]-4-oxo-1H-pyrazolo[4',3':5,6]pyrido[4,3-d]pyrimidin-2-yl]-4-propoxyphenyl]sulfonyl]pyrrolidine;

(3R)-3-(dimethylamino)-1-[[3-[5-[[(4-fluorophenyl)methyl]amino]-4,8-dihydro-8-[(4-methoxyphenyl)methyl]-4-oxo-1H-pyrazolo[4',3':5,6]pyrido[4,3-d]pyrimidin-2-yl]-4-propoxyphenyl]sulfonyl]pyrrolidine;

(3R)-1-[[3-[5-[[(3-chloro-4-methoxyphenyl)methyl]amino]-4,8-dihydro-4-oxo-1H-pyrazolo[4',3':5,6]pyrido[4,3-d]pyrimidin-2-yl]-4-propoxyphenyl]sulfonyl]-3-(dimethylamino)pyrrolidine; and (3R)-3-(dimethylamino)-1-[[3-[5-[[(4-fluorophenyl)methyl]amino]-4,8-dihydro-4-oxo-1H-pyrazolo[4',3':5,6]pyrido[4,3-d]pyrimidin-2-yl]-4-propoxyphenyl]sulfonyl]pyrrolidine;

or a pharmaceutically-acceptable salt of a compound selected from the above compounds.

12. A compound having the formula,

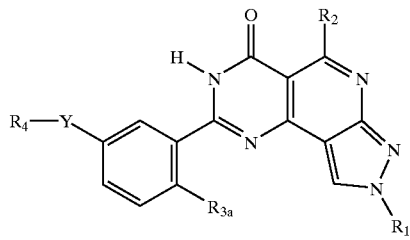

or a pharmaceutically-acceptable salt thereof:
wherein:
R$_1$ is hydrogen, alkyl, or alkylaryl, the aryl of said alkylaryl being optionally-substituted with OR$_8$;
R$_2$ is hydrogen, halogen, —OR$_5$ or —NHR$_6$;
R$_{3a}$ is —O-alkyl or —O-substituted alkyl;
R$_4$ is five or six-membered heterocyclo, said heterocycle being optionally-substituted with alkyl, NH$_2$, NH(alkyl), or N(alkyl)$_2$;
R$_6$ is hydrogen, alkyl or alkylaryl, the aryl of said alkylaryl being optionally-substituted with halogen, hydrogen, or alkoxy;
R$_8$ is hydrogen or alkyl; and
Y is —SO$_2$— or —(C=O)—.

13. A pharmaceutical composition comprising one or more compounds according to claim 1, or a pharmaceutically-acceptable salt thereof in a pharmaceutically-acceptable carrier.

14. A pharmaceutical composition comprising at least one compound of claim 1, or a pharmaceutically-acceptable salt thereof, in combination with at least one other therapeutic agent selected from one or more of a GMP PDE 5 inhibitor, modulator of the large-conductance calcium-activated potassium (BK) channel, prostanoid, α-adrenergic agonist, endothelin antagonist, angiotensin II (especially, subtype AT$_1$) antagonist, angiotensin converting enzyme inhibitor, renin inhibitor, and serotonin (5-HT$_{2c}$) agonist, in a pharmaceutically-acceptable carrier. carrier.

15. A method of treating a condition in a mammal comprising administering to the mammal in need thereof a therapeutically-effective amount of one or more compounds according to claim 1, or a pharmaceutically-acceptable salt thereof, wherein the condition is selected from cardiovascular diseases comprising hypertension, angina (stable, unstable, and variant), heart failure, restenosis, atherosclerosis, dyslipidemia, blood vessel patency, thrombus (venous and arterial), myocardial infarction, peripheral vascular disease, stroke, bronchitis, chronic asthma, allergic asthma, allergic rhinitis, glaucoma, and benign prostate hyperplasia (BPH); sexual dysfunction in men and women; diabetes mellitus and diseases of the gastrointestinal tract comprising disorders of gut motility and gastric paresis.

16. A method of treating a condition in a mammal according to claim 15, comprising administering to the mammal in need thereof a therapeutically-effective amount of composition of claim 13 simultaneously or sequentially with a second composition containing another agent selected from one or more of a GMP PDE 5 inhibitor, modulator of the large-conductance calcium-activated potassium (BK) channel, prostanoid, α-adrenergic agonist, endothelin antagonist, angiotensin II (especially, subtype AT$_1$) antagonist, angiotensin converting enzyme inhibitor, renin inhibitor, and serotonin (5-HT$_{2c}$) agonist.

17. A method of treating a cardiovascular disorder in a mammal comprising administering to the mammal in need thereof a therapeutically-effective amount of a composition according to claim 13.

18. A method of treating sexual dysfunction in a male or female mammal comprising administering to the mammal in need thereof a therapeutically-effective amount of a composition according to claim 13.

19. A method of treating diabetes in a mammal comprising diabetes mellitus comprising administering to the mammal in need thereof a therapeutically-effective amount of a composition according to claim 13.

20. A method of treating a gastrointestinal disorder in a mammal comprising gastric paresis comprising administering to the mammal in need thereof a therapeutically-effective amount of a composition according to claim 13.

* * * * *